(12) United States Patent
McGrath et al.

(10) Patent No.: US 6,703,202 B2
(45) Date of Patent: Mar. 9, 2004

(54) EVALUATING AND PREDICTING CLINICAL OUTCOMES BY GENE EXPRESSION ANALYSIS

(75) Inventors: Michael McGrath, Burlingame, CA (US); Stefan Meuer, Heldelberg (DE); Friedrich-Wilhelm Kuehne, Bangkok (TH)

(73) Assignee: Oxo Chemie AG, Fribourg (CH)

( * ) Notice: Subject to any disclaimer, the term of this patent is extended or adjusted under 35 U.S.C. 154(b) by 0 days.

(21) Appl. No.: 09/725,499

(22) Filed: Nov. 30, 2000

(65) Prior Publication Data

US 2001/0036631 A1 Nov. 1, 2001

Related U.S. Application Data

(60) Provisional application No. 60/167,911, filed on Nov. 30, 1999.

(51) Int. Cl.[7] .......................... C12Q 1/68; C12P 19/34; C07H 21/04; C07H 21/02
(52) U.S. Cl. .................. 435/6; 435/91.1; 435/91.2; 536/24.3; 536/24.32; 536/24.33; 536/23.1
(58) Field of Search .................. 435/6, 91.1, 91.2; 514/661; 536/24.3, 24.33; 424/9.1, 9.2

(56) References Cited

U.S. PATENT DOCUMENTS

| | | | | |
|---|---|---|---|---|
| 5,877,222 A | * | 3/1999 | McGrath | 514/661 |
| 5,965,421 A | | 10/1999 | Ni et al. | 435/194 |

FOREIGN PATENT DOCUMENTS

| | | |
|---|---|---|
| WO | WO 9914237 | 3/1999 |

OTHER PUBLICATIONS

Raffanti et al., "Randomized, Double–Blind, Placebo–Controlled Trial of the Immune Modulator WF10 in Patients with Advanced AIDS*", Infection, vol 26, No. 4, pp. 202–206 (1998).*

Paturel et al., "Quantitative Analysis of Th1, Th2 And TGF–B1 Cytokine Expression In Tumor, TIL And PBL of Non–Small Cell Lung Cancer Patients", Int. K. Cancer, vol. 77, pp. 7–12, (1998).*
Baan et al., "Intragraft IL–4 mRNA expression os associated with down–regulation of liver graft rejection", Clin. Transplataion, vol. 10, pp. 542–549, (1996).*
Kohne et al., "Long–Term Survival Of A Stage D Prostate Cancer", Aktuelle Urologie, vol. 29, No. 5, pp. 261–263, (1998).*
Asselin–Paturel, et al., "Quantitative Analysis of Th1, Th2 and TGF–B1 Cytokine Expression in Tumor, TIL and PBL of Non–Small Cell Lung Cancer Patients", Int. J. Cancer, vol. 77, 1998, pp. 7–12.
Stoetzer, et al., "Association of bcl–2, bax, bcl–xL and Interleukin–1–b–converting Enxyme Expression With Initial Response to Chemotherapy in Acute Myeloid Leukemia", Leukemia, vol. 10, No. suppl. 3, 1996, pp. s18–s22.
Shi, et al., "Expression of Thyrotrophin Receptor Gene in Thyroid Carcinoma is Associated With a Good Prognosis", Clinical Endocrinology, vo. 39, 1993, pp. 269–274.
Wong, et al., "Evidence for Rantes, Monocyte Chemotactic Protein–1, and Macrophage Inflammatory Protein–1b Expression in Kawasaki Disease", The Journal of Rheumatology, vol. 24, No. 6, Jun. 1997.
Raffanti, S.P. et al., "Randomized Double–Blind, Placebo–Cnotrolled Trial of the Immune Modulator WF10 in Patients With Advanced AIDS", Infection, vol. 26, No. 4, Jul. 1998, pp. 202–207.

* cited by examiner

*Primary Examiner*—Gary Benzion
*Assistant Examiner*—Cynthia Wilder
(74) *Attorney, Agent, or Firm*—Heller Ehrman White and McAuliffe

(57) ABSTRACT

Methods of determining clinical outcomes in patients suffering from a pathological condition or syndrome are provided. Levels of intracellular gene expression re measured from a clinical sample provided by the patient, and the levels are compared to reference levels. Deviations from reference levels are predictive of clinical outcomes, for example, disease progression or response to therapeutic intervention.

16 Claims, 11 Drawing Sheets

Figure 1: Balanced Macrophage Activation Cycle
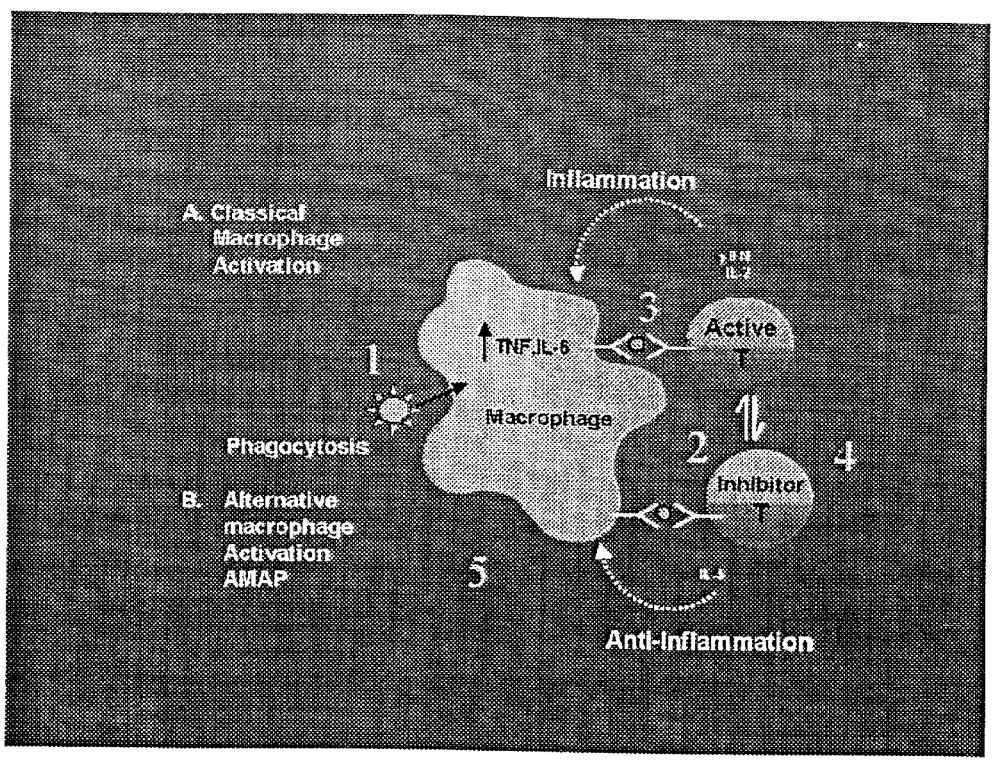

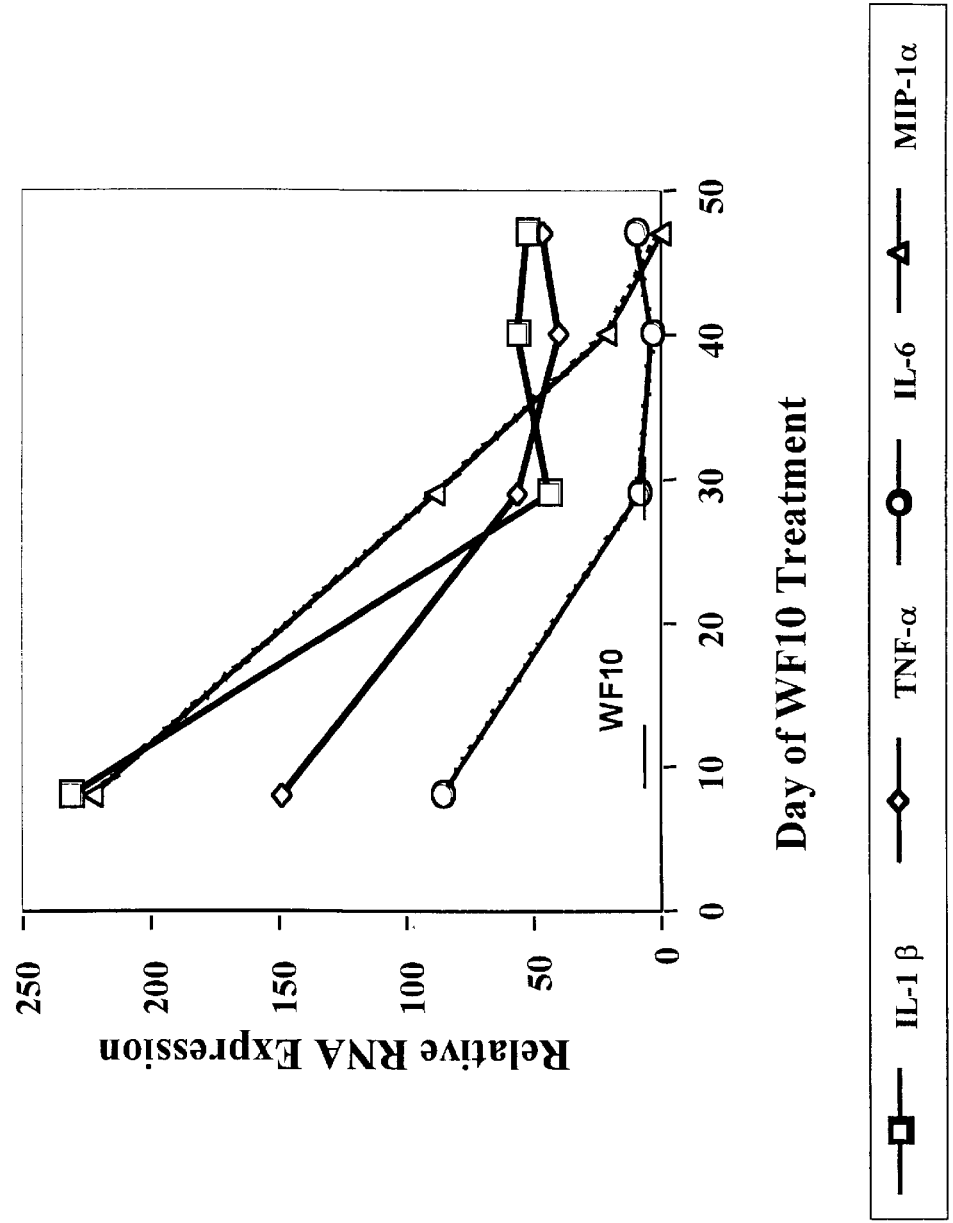
Figure 2: PBMC Inflammatory gene expression after WF10:
Patient 14 (CD8/38 decrease)

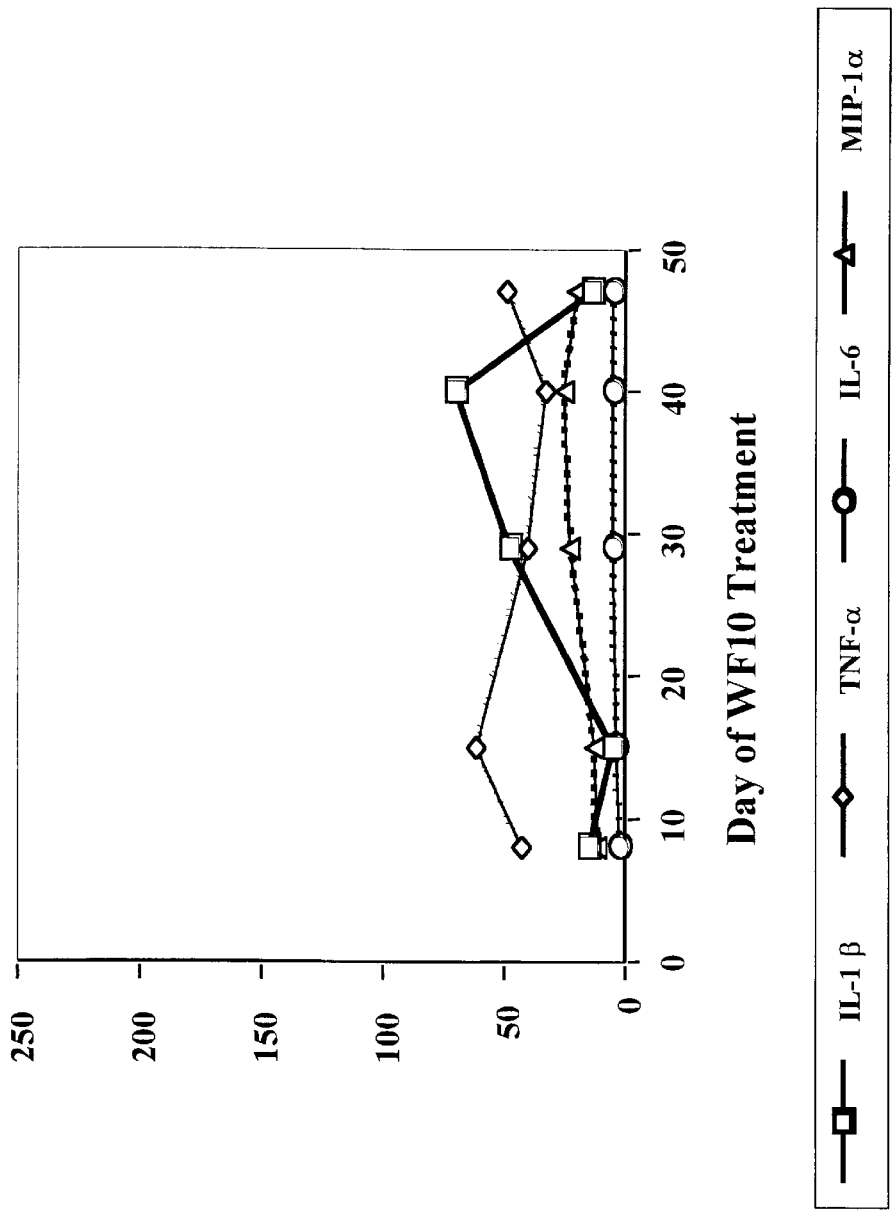
Figure 3: PBMC Inflammatory gene expression after WF10: Patient 15 (CD8/38 unchanged)

Figure 4. Clinical and laboratory characteristics of studied patients

| Patient ID | Age | Sex | Risk Group | Clinical Status | HBV Sero+ | HCV (RNA copy # x 10⁵) | HCV Genotype | ALT*** | Liver Biopsy Inflammation Grade |
|---|---|---|---|---|---|---|---|---|---|
| Acute HCV | 37 | M | IVDU | Fatigue | − | >10.00 | NA | 73** | NA |
| HCV 1 | 45 | M | IVDU | Fatigue/depression | + | 8.3 | 1a | 51 | 1.5 |
| HCV 2 | 66 | F | NA* | NA | − | 14.6 | NA | 22 | 2 |
| HCV 3 | 49 | F | NA | Fatigue, joint pain | + | 10.2 | 1b | 18 | 1 |
| HCV 4 | 52 | F | None | NA | NA | >10.0 | 1 | 71 | 3 |
| HCV 5 | 51 | M | NA | Anxiety | − | 7.52 | 1a | 47 | 2 |
| HCV 6 | 23 | F | IVDU | Psoriasis | − | 7.31 | 3a | 48 | 1.5 |
| HCV 7 | 33 | M | IVDU | Fatigue | + | 6.9 | 1a | 55 | 1 |
| HCV 8 | 30 | F | IVDU | Fatigue | + | 10.0 | NA | 38 | 1 |

NA:  not available

\*    2 weeks earlier peaked at 677

\*\*\*  Alanine amino transferase, normal < 30μ

Figure 6a. Unstimulated - Baseline

| Patient ID | IL-1β | | TNF-α | | IL-2 | IFN-γ | | IL-8 | | IP-10 | | TGF-β | | MiP-1α | | MiP-2α | | IL-10 | | MCSF | | MRP-14 | |
|---|---|---|---|---|---|---|---|---|---|---|---|---|---|---|---|---|---|---|---|---|---|---|---|
| HCV 1 | 1436 | (1) | 597 | (2) | 1 | 75 | (7) | 2152 | (0) | 485 | (4) | 4559 | (2) | 806 | (0) | 89 | (0) | 4 | (0) | 31 | (19) | 7107 | (1) |
| HCV 2 | 35829 | (18) | 5752 | (20) | 0 | 41 | (4) | 6007 | (1) | 8581 | (78) | 3867 | (2) | 27703 | (13) | 758 | (3) | 0 | (ND) | 136 | (86) | 56597 | (3) |
| HCV 3 | 5362 | (3) | 732 | (3) | 0 | 86 | (7) | 2430 | (0) | 0 | (ND) | 1303 | (1) | 1876 | (1) | 764 | (3) | 0 | (ND) | 35 | (22) | 235 | (0) |
| HCV 4 | 12354 | (6) | 14832 | (52) | 219 | 518 | (45) | 43980 | (8) | 1530 | (14) | 2137 | (1) | 84235 | (39) | 7148 | (26) | 9 | (1) | 200 | (126) | 68061 | (6) |
| HCV 5 | 3301 | (2) | 1664 | (6) | 0 | 492 | (43) | 5720 | (1) | 1098 | (10) | 2092 | (1) | 3082 | (1) | 1565 | (6) | 44 | (4) | 88 | (56) | 15613 | (1) |
| HCV 6 | 219 | (0) | 312 | (1) | 2 | 85 | (7) | 6010 | (1) | 396 | (4) | 3246 | (1) | 3692 | (2) | 370 | (1) | 1 | (0) | 27 | (17) | 87637 | (7) |
| HCV 7 | 5996 | (3) | 457 | (2) | 0 | 26 | (2) | 3327 | (1) | 23 | (0) | 2088 | (1) | 4487 | (2) | 842 | (3) | 14 | (1) | 72 | (45) | 2756 | (0) |
| HCV 8 | 1286 | (1) | 522 | (2) | 0 | 465 | (40) | 1897 | (0) | 956 | (9) | 2739 | (1) | 1524 | (1) | 243 | (1) | 24 | (2) | 99 | (62) | 18209 | (2) |
| Normal (range) | 1944 | (0-3.11) | 283 | (.12-2.56) | 2 (0-5.5) | 12 | (.23-2.69) | 5761 | (0-4.5) | 111 | (.04-2.81) | 2300 | (.08-1.92) | 2169 | (.09-2.65) | 278 | (0-2.71) | 11 | (.27-2.64) | 2 | (.50-1.50) | 11987 | (.37-2.74) |

Figure 6b. PMA/Iono – Induced

| Patient ID | IL-1β | TNF-α | IL-2 | IL-4 | IFN-γ | IL-8 | IP-10 | TGF-β | MiP-1α | MiP-2α | IL-10 | MCSF | MRP-14 |
|---|---|---|---|---|---|---|---|---|---|---|---|---|---|
| HCV 1 | 2451 (.91) | 4497 (.46) | 11284 (.48) | 2153 (1.55) | 31312 (.70) | 63649 (1.25) | 244 (1.86) | 14895 (3.82) | 13664 (.45) | 4044 (1.07) | 179 (.17) | 936 (2.92) | 10135 (1.65) |
| HCV 2 | 7723 (2.87) | 1076 (.11) | 284 (.01) | 2953 (2.13) | 1509 (.03) | 90864 (1.79) | 123 (.94) | 3663 (.94) | 21819 (.72) | 8958 (2.37) | 0 (ND) | 1995 (6.23) | 28444 (4.64) |
| HCV 3 | 4978 (1.85) | 2917 (.30) | 1614 (.07) | 234 (.17) | 7269 (.16) | 3203 (.06) | 134 (1.02) | 1655 (.42) | 8592 (.28) | 891 (.24) | 43 (.04) | 217 (.68) | 167 (.03) |
| HCV 4 | 3499 (1.30) | 25821 (2.62) | 23164 (.98) | 3934 (2.84) | 47709 (1.07) | 54527 (1.07) | 241 (1.84) | 3090 (.79) | 157822 (5.21) | 19113 (5.06) | 15 (.01) | 523 (1.63) | 62887 (10.27) |
| HCV 5 | 5983 (2.23) | 7535 (.77) | 3440 (.15) | 646 (.47) | 8343 (.19) | 42353 (.83) | 73 (.56) | 2284 (.59) | 27386 (.90) | 13348 (3.54) | 79 (.08) | 471 (1.47) | 16828 (2.75) |
| HCV 6 | 244 (.09) | 1740 (.18) | 3895 (.16) | 1469 (1.06) | 4914 (.11) | 21428 (.42) | 920 (7.03) | 3185 (.82) | 18177 (.60) | 4187 (1.11) | 5 (.01) | 192 (.60) | 40428 (6.60) |
| HCV 7 | 5989 (2.23) | 342 (.03) | 6 (0) | 204 (.15) | 156 (0) | 8209 (.16) | 28 (.22) | 2289 (.59) | 4109 (.14) | 2168 (.57) | 0 (ND) | 290 (.91) | 1262 (.21) |
| HCV 8 | 1199 (.45) | 4374 (.44) | 2606 (.11) | 1486 (1.07) | 10248 (.23) | 37248 (.73) | 23 (.17) | 3384 (.87) | 11970 (.39) | 5001 (1.33) | 225 (.22) | 1498 (4.68) | 26243 (4.28) |
| Normal (range) | 2689 (0-2.77) | 9839 (.13-2.40) | 23672 (.23-2.70) | 1385 (.10-2.24) | 44756 (.26-2.83) | 50757 (.02-4.82) | 131 (0-2.90) | 3897 (.03-4.15) | 30306 (.12-2.10) | 3774 (.07-2.04) | 1022 (.09-5.84) | 22 (.55-1.32) | 6125 (.08-2.72) |

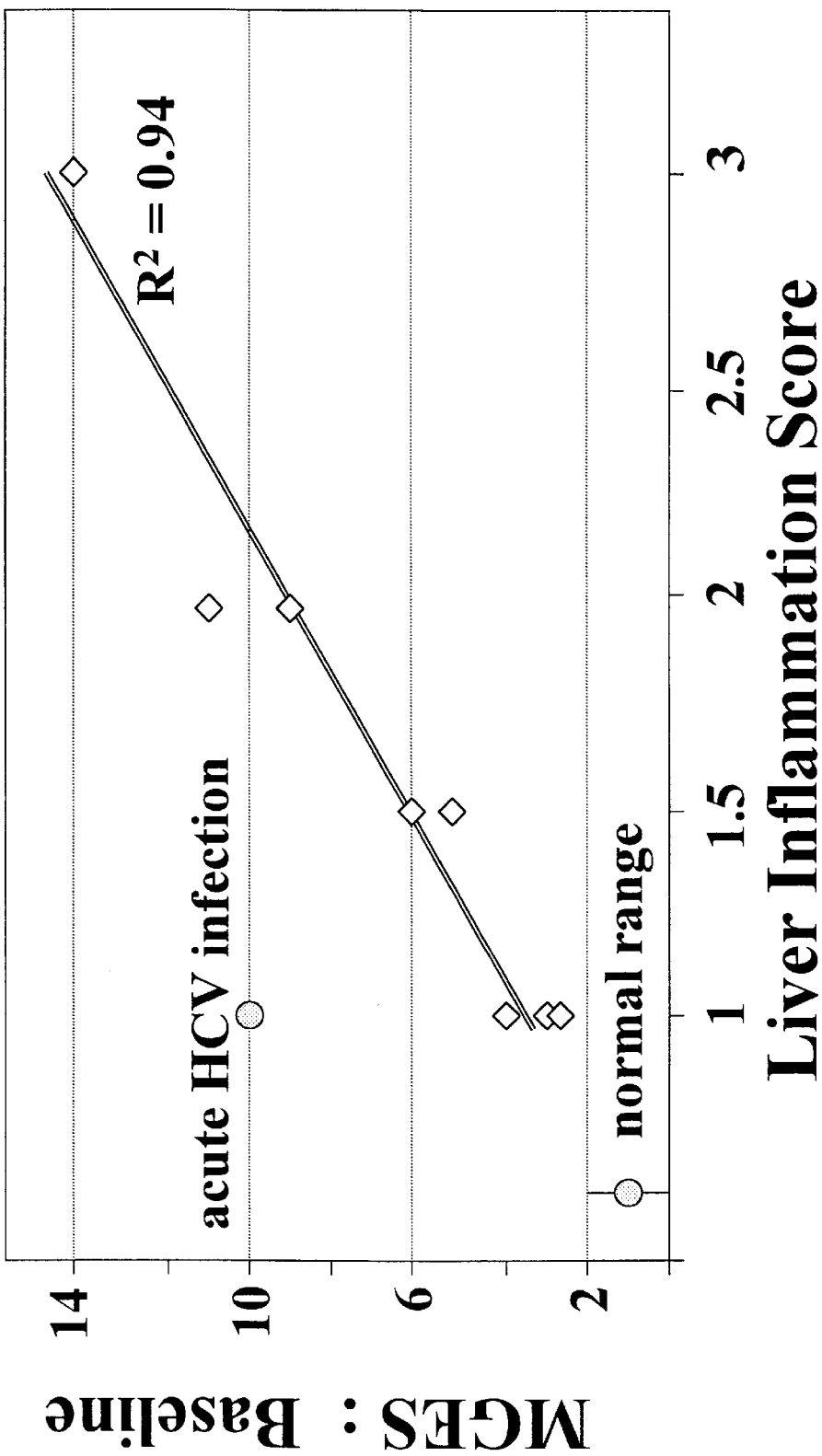
Fig. 8: Multi-gene expression score in unstimulated PBMC of patients with HCV disease

Figure 9. MGES value calculations

|  | GES score | MGES value |
|---|---|---|
| Baseline* | 0 – 1.5 | 0 |
|  | 1.5 – 3 | 1 |
|  | 3 – 10 | 2 |
|  | >10 | 3 |
| Induced** | <0.1 | -3 |
|  | 0.10 – 0.25 | -2 |
|  | 0.25 – 0.75 | -1 |
|  | 0.75 – 1.5 | 0 |
|  | 1.5 – 3 | 1 |
|  | 3 – 10 | 2 |
|  | >10 | 3 |

\* TNF-α, IP-10, MIP-2α, IFN-γ, MRP-14
\*\* TNF-α, MIP-2α, IL-2
All values added together for final MGES/specimen

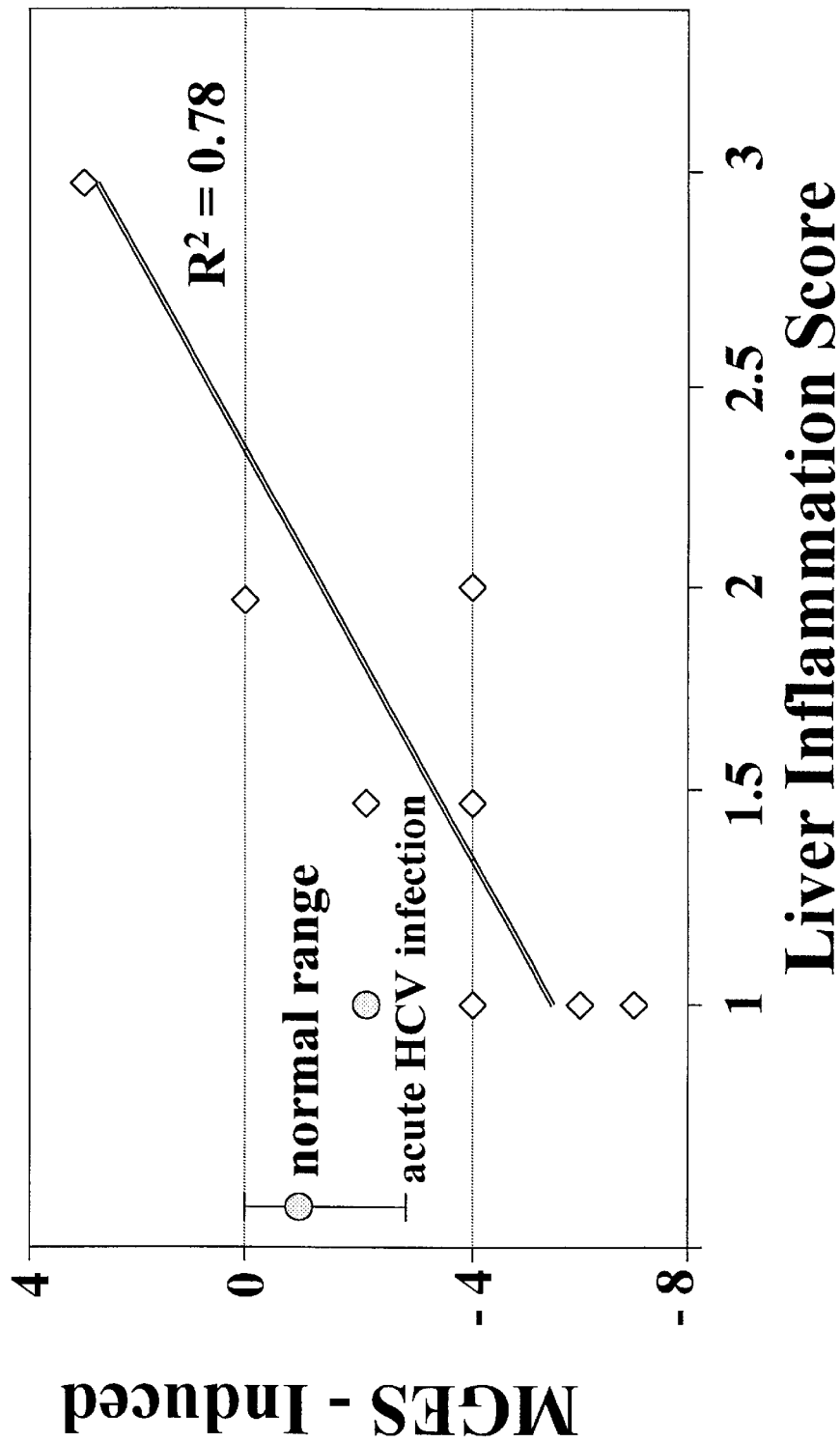
Fig. 10: Multi-gene expression score in PMA stimulated PBMC of patients with HCV disease

EVALUATING AND PREDICTING CLINICAL OUTCOMES BY GENE EXPRESSION ANALYSIS

This application claims the benefit of Provisional Application No. 60/167,911, filed Nov. 30, 1999.

FIELD OF THE INVENTION

The present invention relates to methods for evaluating and predicting clinical outcomes in patients by measuring levels of gene expression. Methods are provided for quantitating gene expression levels, and the measured levels are compared against reference levels. Deviations from the reference levels can be correlated with clinical outcomes. For example, the type and extent of a patient's response to a therapeutic intervention can be determined, or the prognosis for a patient's survival can be estimated. The gene expression levels can be measured in essentially any chosen body tissue or fluid. Surprisingly, it has been found that measurement of intracellular gene expression levels in blood are indicative of clinical outcomes.

BACKGROUND OF THE INVENTION

Methods for examining overall gene expression in, for example, disease states, previously have been described. See, for example, U.S. Pat. No. 5,874,219; Zakut et al., *Cancer Research,* 53:5–8 (1993); Mohaupt et al., *Kidney International,* 46:653–665 (1994); Liang and Pardee (1992) *Science* 257, 967–971; Liang et al (1993), *Nucleic Acids Res.* 21, 3269–3275; Bauer et al (1993) *Nucleic Acids Res.* 21, 4272–4280; Stone and Wharton (1994), *Nucleic acid Res.* 22, 2612–2618 and Wang and Feuerstein (1995) *Biotechniques* 18, 448–452; WO 93/18176 and DE 43 17 414. These methods, however, generally provide a "snapshot" of gene expression that is qualitative, rather than quantitative. Accordingly, the methods provide an indication only of whether a gene is being expressed at a detectable level in a particular tissue. Moreover, even when applied to samples from patients suffering from a pathological syndrome, none of these methods provides any correlation with clinical outcome for the patient. It is apparent, therefore, that new and improved methods for measuring levels of gene expression and correlating those levels with clinical outcome are greatly to be desired.

SUMMARY OF THE INVENTION

There exists a need to determine and predict clinical outcomes in patients It is therefore an object of the invention to provide methods for evaluating (e.g., determining and/or predicting) clinical outcome for a patient suffering from a clinical condition or syndrome, comprising the steps of (a) providing a clinical specimen obtained or derived from the patient, (b) measuring the levels of expression of a preselected set of genes in the clinical specimen; and (c) comparing said levels of expression against a set of reference expression levels, where a deviation of the level of expression of one or more of the preselected set of genes is indicative of clinical outcome for the patient. The phrase "preselected gene(s)" refers to genes that have been determined to be suitable in practice of the invention. Preferably, in accordance with practice of the invention, such genes are selected where there is a correlation between the level of gene expression and the nature and extent of a disease state or other undesired condition.

In accordance with one aspect of the invention, the clinical specimen is a sample of blood, tissue, or cerebrospinal fluid. The clinical specimen may be a sample of blood, and derived therefrom, such as plasma or serum sample or fraction.

In accordance with another aspect of the invention, the expression levels of at least three preselected genes are measured. In one embodiment, the expression level of at least one proinflammatory cytokine is measured. In another embodiment, the expression level of at least three preselected proinflammatory cytokines is measured. In yet another embodiment, the preselected proinflammatory cytokine genes are selected from the group consisting of TNF-$\alpha$, IL-6, IL-1, IL-8, IP-10 and MIP-1$\alpha$.

In accordance with another aspect of the invention, the clinical condition or syndrome is an inflammatory disorder. In one embodiment, the inflammatory disorder is a chronic inflammatory disorder. In another embodiment, the chronic inflammatory disorder is selected from the group consisting of chronic hepatitis, hepatitis B and C, chronic obstructive pulmonary disease, inflammatory mucosal disease, autoimmune disease, dementia, cardiovascular disease, and cancer. The inflammatory mucosal disease may be selected from the group consisting of inflammatory bowel disease, Crohn's disease, and colitis. The dementia may be AIDS-related dementia or Alzheimer's disease. The cancer may be selected from the group consisting of lymphoma, prostate cancer, and colon cancer. In another embodiment, the clinical condition is transplant rejection in a patient with an allograft. The allograft may be a heart, liver, kidney, or other organ.

In accordance with still another aspect of the invention, the clinical outcome that is determined is response to a therapeutic intervention. The therapeutic intervention may be treatment with a drug. The drug may be a stabilized chlorite solution. In particular, the stabilized chlorite solution may be WF-10.

In accordance with yet another aspect of the invention, the clinical condition or syndrome is HIV infection. In one embodiment, the clinical condition or syndrome is AIDS.

In accordance with a still further aspect of the invention, the indicated clinical outcome is the probability of patient survival at a predetermined date. In one embodiment, the indicated clinical outcome is the probability of patient survival after six months.

In accordance with a further aspect of the invention, the levels of gene expression are measured by a quantitative polymerase chain reaction. The polymerase chain reaction may be a reverse transcriptase/polymerase chain reaction. The polymerase chain reaction may be carried out using fluorescent detection of the amplification products. In one embodiment, the polymerase chain reaction may be carried out using a LightCycler® instrument, or using other appropriate technology.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1 shows a schematic of a macrophage activation cycle wherein multiple steps occur during various forms of activation and recycling of macrophage function so as to achieve Balanced Macrophage Activation.

FIG. 2 shows the changes in gene expression of proinflammatory cytokines in a patient (#14) after treatment with WF10. The levels are reduced, indicating a good prognosis and good response to treatment.

FIG. 3 shows the changes in gene expression of proinflammatory cytokines in a patient (#15) after treatment with WF10. The levels are low to begin with, and are unchanged with treatment, indicating that therapy is unnecessary and that the patient has a good prognosis.

FIG. 4 summarizes characteristics of the patients studied in Example 2. Patients were being enrolled in a prospective Phase II study evaluating the potential of WF10 for treatment of HCV disease. Baseline blood specimens were available from these patients with paired liver biopsies for the study. All patient histories and specimens were obtained in accordance with standard Committee on Human Research approved protocols. The acutely infected patient was not being evaluated for treatment by WF10 but presented to one of the study's referring physicians. That patient's specimens were evaluated with the same human subjects approval criteria. The 8 patients with chronic HCV infection had baseline demographic and laboratory data obtained. The patients were not selected by any criteria except that those patients had blood drawn before enrollment in the WF10 clinical trial and had a liver biopsy performed within 2 weeks of the blood draw. Laboratory values of HCV gene expression levels and liver function tests were also obtained within this same 2-week window of time. Liver biopsies were obtained from the patients evaluated by an independent pathologist, who scored the inflammation grade base on standard 4-point grading system. Only at the end of the gene expression evaluation were all data regarding the liver biopsy, laboratory values, and gene expression values pooled for ultimate data analysis. Only Patient 4 in this study had been treated previously with interferon and Ribivarin and had not received any treatment in the 3-month period prior to entry into the study.

FIG. 6A shows the actual baseline gene expression values and GES for the patients whose data are summarized in FIG. 5.

FIG. 6B shows the actual induced gene expression values and GES for the patients whose data are summarized in FIG. 7.

FIG. 8 shows the multigene expression score in unstimulated PBMC of patients with HCV disease.

FIG. 9 shows the scoring system used in MGES value calculations.

FIG. 10 shows multigene expression score in stimulated PBMC of patients with HCV disease.

DETAILED DESCRIPTION OF THE INVENTION

Figure 5:
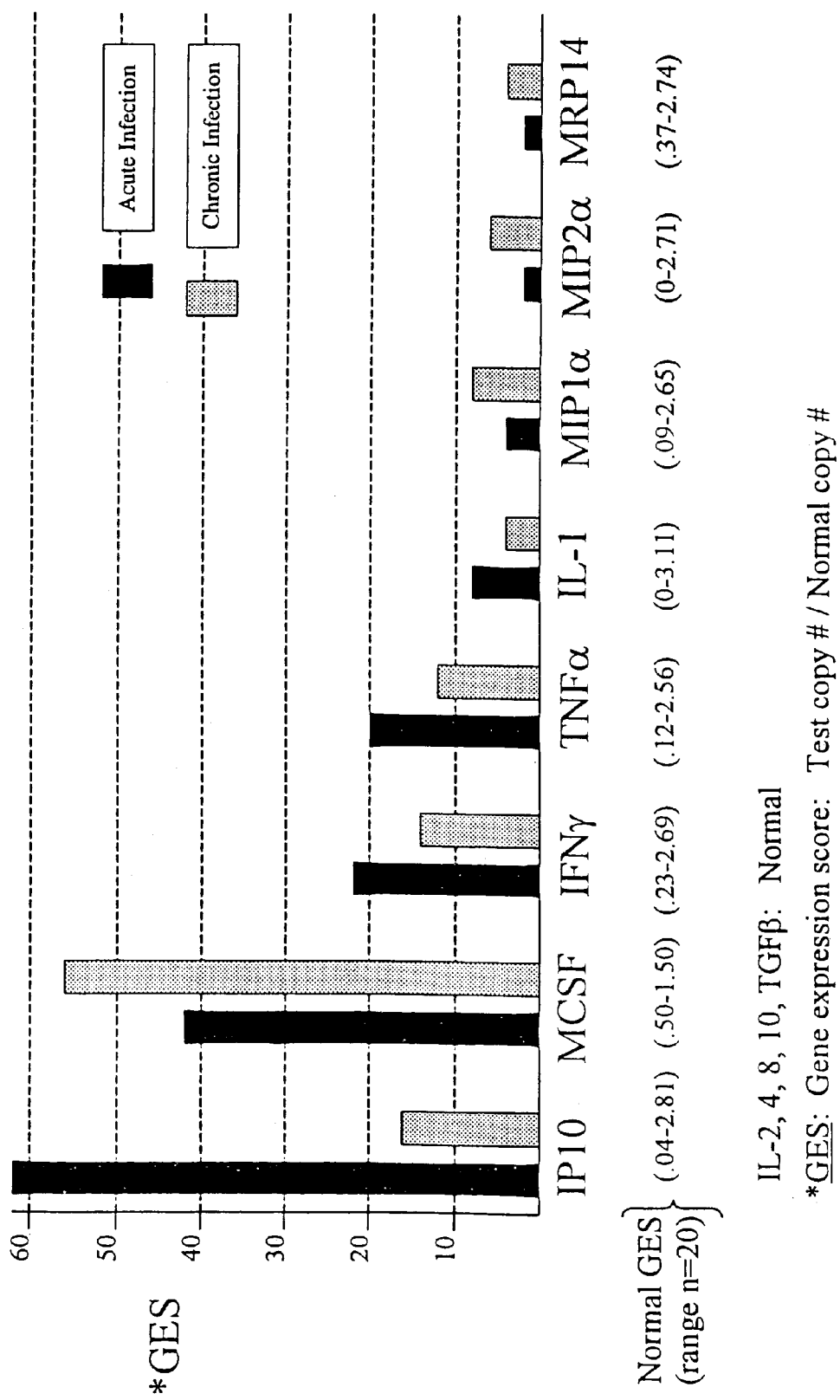
FIG. 5 shows immune activation gene expression in PBMC from patients with acute and chronic HCV infection.

The present invention provides methods of determining clinical outcomes in patients by measuring levels of expression of a preselected set of genes. The gene expression levels are compared to reference standards and deviations from those standards are indicative of clinical outcomes. The gene expression levels can be measured in essentially any clinical specimen, including tissue or fluid, such as cerebrospinal fluid. Surprisingly, however, the inventors have discovered that gene expression levels measured in blood samples are indicative of clinical outcomes. This is surprising because the blood has typically been considered to be a quiescent organ of the body, and that measurement of gene expression levels in the blood has been thought to be an exercise of little or no value. In particular, measurement of intracellular gene expression levels in blood cells can be used. Of course, use of blood makes obtaining and analyzing clinical samples simple, convenient, and minimally invasive.

Measurement of Gene Expression Levels

The gene expression levels used in the methods of the invention can be measured by any method now known or that is devised in the future that can provide quantitative information regarding the levels to be measured. The methods preferably are highly sensitive and provide reproducible results. In one embodiment, methods based upon nucleic acid amplification technologies are used. In particular, methods based upon the polymerase chain reaction ("PCR") and related amplification technologies, such as NASBA and other isothermal amplification technologies, may be used. More particularly, so called "RT-PCR" methods using reverse transcription of mRNA followed by amplification of the resulting cDNA are contemplated.

Methods for carrying out quantitative PCR are known in the art. See, for example, U.S. Pat. Nos. 5,210,015 and 5,487,972 and EP 512334B1 which are hereby incorporated by reference in their entirety. Commercial instruments for carrying out quantitative PCR and RT-PCR are available from PE Applied Biosystems, 850 Lincoln Centre Drive, Foster City, Calif. 94404, from Roche Molecular Systems, Inc., 1145 Atlantic Avenue, Alameda, Calif. 94501, and from Roche Molecular Biochemicals, Indianapolis, Ind. In a particular embodiment, the LightCycler instrument from Roche Molecular Biochemicals is used. This instrument can be used following the manufacturer's instructions as described below. Primer sets for amplification of any known gene can be designed using methods that are well known in the art, for example, using gene sequences from public databases such as GENBANK and using primer design software such as OLIGO. Primer sets for many genes also are commercially available, for example from PE Applied Biosystems, Roche Molecular Biochemicals, Roche Diagnostics, and Search-LC (Heidelberg, Germany).

Samples for Measuring Gene Expression Levels

Any conveniently available tissue sample from a patient can be used for measurement of gene expression levels. In particular embodiments, the sample can be blood, cerebrospinal fluid, and cellular tissue derived from biopsy or from exfoliation such as from the cheek wall. In one embodiment, the sample is peripheral blood mononuclear cells, which are readily and easily available via minimally invasive methods. Methods for preparing the sample for gene expression analysis are well known in the art, and can be carried out using commercially available kits.

Determining Clinical Outcomes

The gene expression levels obtained preferably are compared and normalized against reference genes in the same sample. Typically, "housekeeping" genes such as actin, are used for this normalization. Other "housekeeping" genes are well known in the art, such as HPRT, CPB, and G6PD.

For determining clinical outcomes, the gene expression levels obtained from the clinical sample (from the "test patient") are compared to levels in reference samples. The reference samples typically are obtained from healthy individuals who are disease free, or who are not suffering from the same pathological condition or syndrome as the test patient. Preferably, expression levels of the genes of interest are determined from a number of healthy individuals, and an average or mean is obtained. In a particular embodiment, the reference levels may be determined from individuals of the same sex and age as the test patient. In another embodiment, the reference levels may be obtained from tabulated data, where those data are compiled from healthy patients of appropriate sex and age.

The relative levels of gene expression that can be predictive (a type of indication) of clinical outcome can be higher or lower levels of expression. For example, it is shown below that increased levels of expression of proinflammatory cytokines, such as TNF-α, IL-6, IL-1, IL-8, IP-10 and MIP-1α are reflective of a poor clinical outcome (for example, reduced expectation for long-term survival) for patients infected with HIV. When the patient is treated with an anti-HIV compound, the relative levels of the proinflammatory cytokines can be measured again. If the levels of the cytokines is reduced, this indicates that the patient is responding well to the treatment. In this case, the clinical outcome may be that the patient can cease anti-HIV therapy, or reduce the dose of the anti-HIV compound. A lack of response can indicate that the patient will not respond to therapy, and therefore has a poor prognosis, or that the dose of anti-HIV compound must be increased, or additional therapeutic interventions must be used. A lack of response also may indicate that the progression of the disease has not been halted or slowed by therapy.

Although the present invention specifically contemplates that the levels of proinflammatory cytokine expression can be measured and used to predict clinical outcome, the skilled artisan will recognize that the invention is not so limited. Thus, methods for identifying changes in gene expression are well known in the art, as described supra. Even though these methods are not sufficiently quantitative for use in the present invention, they can be used to predict those genes whose expression is changed in a disease state. Quantitative measurements, such as quantitative RT-PCR can then be used to measure the changes in gene expression. Those changes can be tracked in patients and correlated with clinical outcomes by methods that are well known in the art.

Thus, for any given disease, a predictive method for determining clinical outcome can be developed. The discussion below describes the gene expression levels in macrophage activation, and describes how those levels, and their change upon treatment with a particular drug (WF10) provide information regarding clinical outcomes in patients suffering from chronic inflammatory disease, such as chronic hepatitis, hepatitis B and C, chronic obstructive pulmonary disease, inflammatory mucosal disease, autoimmune disease, dementia, cardiovascular disease, and cancer. The inflammatory mucosal disease may be selected from, for example, inflammatory bowel disease, Crohn's disease, and colitis. The dementia may be, for example, AIDS-related dementia or Alzheimer's disease. The cancer may be, for example, lymphoma, prostate cancer, or colon cancer. Example 2 below also demonstrates that the methods of the invention can be used to predict clinical outcome in patients suffering from hepatitis C. The methods of the invention may also be used to detect or predict clinical outcome of transplant rejection in patients receiving allografts, such as heart, liver, kidney, or other organs. Thus, measurement of altered, particularly increased, inflammatory cytokine gene expression is indicative of rejection of the allograft. Particular gene expression levels that can be measured to detect allograft rejection include IP10, TNFα, δ-IFN, and other macrophage inflammation genes.

Activation of Macrophages

WF10 is a stabilized chlorite matrix approved for clinical use in a systemic form (WF10) and in a more dilute topical form (Oxoferrin) See Kühne, *Die erwünschte Sauerstoffaktivierung, dokumentiert am Beispiel der Wundheilung: der Weg zur Oxoferin-Therapie*. In: Elsmer E. F., Bors W., Wilmanns W. (eds.): Reaktive Sauerstoffspezies in der Medizin. Springer Verlag, Berlin 1986, pp. 5–15. WF10 has been approved in Thailand for systemic administration to patients with post-radiation syndrome and for supportive care in patients being treated for cancer. These indications have been studied extensively and reviewed. See Raffanti et al., *Infection* 26:201–206 (1998). Oxoferrin is used topically to enhance healing of chronic wounds such as diabetic ulcers. Hinz et al., *Lancet* 1: 825–828 (1986). The major target cells in the body for WF10 reactivity are the macrophage and dendriticcell populations. They will be referred to simply as macrophages as both cell populations are derived from common precursor cells. The in vitro and clinical effects of WF10 are best understood in the context of the newly proposed balanced-macrophage activation theory. FIG. 1 shows a schematic of a macrophage activation cycle wherein multiple steps occur during various forms of activation and recycling of macrophage function so as to achieve Balanced Macrophage Activation. Each step in the macrophage activation cycle is numbered (1–5) and is described sequentially.

1. The first thing that occurs in a macrophage activation program is phagocytosis of foreign material. Macrophages engulf pathogenic organisms such as bacteria, fungi and viruses. This is one of the oldest and most important functions of macrophages and is how the macrophage derived its name. "Macro" meaning big, and "phage" meaning eater, thereby conferring on the macrophage the term "Big Eater." Upon successful phagocytosis of a foreign substance, the macrophage processes this material through a proteolytic pathway, cutting individual proteins into small peptides that then are involved in the second step of macrophage activation.

2. Antigen presentation: After foreign materials have been cut into peptides, macrophages present antigen to T lymphocytes utilizing the major histocompatibility antigens class 1 (HLA) and class 2 (DR) and initiate expansion of a normal immune response. T cell activation predominantly occurs through this antigen-presenting-cell function. Standard cytotoxic T cells specific for virus infected cells, cancers or fungi are developed that ultimately lead to successful immunologic clearance of those foreign processes. This is represented in FIG. 1 as an active immune response. Upon successful activation of an active immune response, T cells express various activation antigens such as CD38 and secrete factors such as interleukin-2 (IL-2). IL2 allows T cells to proliferate and gamma-interferon (γ-IFN) to cause further macrophage activation and step 3.

3. Classical macrophage activation: A product of T cell activation, gamma-interferon induces full inflammatory changes and classical macrophage activation. This activation causes upregulation of inflammatory cytokines such as IL1, IL6, and tumor necrosis factor (TNF). The macrophage in this state is extremely inflammatory and causes secondary effects such as fevers, and when chronically stimulated, weight loss and further non-specific activation of immunologic responses.

4. TH1 to TH2 (Active to Inhibitor T) shift: During the initiation of a cellular response which ultimately leads to production of cytotoxic T cells and T cells producing IL2 (TH1 cell), a second major class of T cell, the TH2 cell, is induced which is involved in both B cell activation as well as providing signals for the balanced macrophage activation. Cytokines produced by the TH2 cells include IL4, IL5, IL6, and IL10. These factors cause B cell activation, B cell proliferation, hypergammaglobulinemia, up-regulation of IgE and allergic reactions and eosinophilia. A net result of excess IL10 production is shutting off of step 2 in the response shown in FIG. 1. The TH1 and TH2 cell activation process occur virtually simultaneously in vitro (and likely in vivo), however classical immunologic responsiveness as measured by T cell proliferation in vitro predominantly measures the TH1-like response. The TH2 response has as a key feature, the production of IL4, which is known to activate the alternative macrophage activation pathway (AMAP). (Step 5)

5. AMAP: The Alternative Macrophage Activation Pathway (reviewed in ref. 4) has the following features:
   a. the production of angiogenic factors
   b. inhibition of T cell responses
   c. associated down-regulation of inflammatory-mediator production characteristic of classically-activated macrophages described in step 3.

The Alternative Macrophage Activation Pathway recently has been confirmed as a distinct pathway with the cloning and molecular studies of AMAC-1 (Alternative Macrophage Activation Chemokine-1) (Kodelja et al, *Journal of Immunology* 160:1411–1418 (1998)), also known as macrophage inflammatory protein 4 (MIP-4). Only in macrophages induced to undergo Alternative Macrophage Activation Pathway has the gene AMAC-1/MIP-4 been detected. A secondary byproduct of Alternative Macrophage Activation Pathway is the appearance of phagocytosis in macrophages that have been induced to undergo Alternative Macrophage Activation Pathway induction. This byproduct potentially signals the complete recycling of the Balanced Macrophage Activation pathway.

This scheme, wherein macrophage involvement in immunologic responses goes from steps 1 through 5, is proposed as a cycle in the balanced macrophage activation theory. Because of its cyclic nature, normal immunologic processes do not overemphasize any particular step in the pathway but remain generally in balance.

Diseases Involving Balanced Macrophage Activation Disruption

Balanced Macrophage Activation is disrupted by a variety of pathologic processes and Balanced Macrophage Activation imbalance is responsible for many manifestations of chronic disease. Examples of these imbalances are as follows:

Chronic viral infections: Steps 2 and 3 in FIG. 1 are continually stimulated when a foreign virus cannot be cleared by a successful immune response that would re-establish Balanced Macrophage Activation. This immunologic overstimulation would predictably lead to pathologic sequelae such as cirrhosis and hepatoma in chronic hepatitis B & C infections and profound immune dysregulation in HIV disease. After long periods of time wherein steps 2 and 3 are overemphasized, there would be a predicted shortage of cells to accomplish steps 5 and 1. There also would be an initial overdrive of the TH1 cell population with the appearance of highly activated T cells. An overactivation of step 3 would clinically appear as chronic fever with associated weight loss. Patients with chronic viral infections such as those with HIV also have been observed to have a dramatic TH1 to TH2 shift as described in step 4 for FIG. 1. The Balanced Macrophage Activation theory predicts that this shift is compensatory in nature with the T cells attempting to regulate Balanced Macrophage Activation through production of IL4, the cytokine that normally induces step 5. The conditions suffered by patients with chronic viral diseases would then be byproducts of a chronic inflammatory state. These would include overproduction of inflammatory mediators and inflammatory cytokines that cause secondary immunopathogenic changes. Such changes are observed in HIV disease where excessive inflammatory states drive development of dementia, kidney disease, lymphoma, and wasting syndromes that are secondary to hyperactivity of the macrophage inflammation compartment. A secondary byproduct of chronic viral disease would be the exhaustion of cells in steps 5 and 1 as noted above. This result would decrease the rate of wound healing and decrease associated angiogenesis and phagocytosis. Fewer cells capable of phagocytosing material would allow new infectious organisms such as bacteria and fungus to be poorly cleared by individuals with chronic viral diseases.

Autoimmune disease: Autoimmune diseases are similar to chronic viral diseases in that there is an overstimulation of immunoreactive lymphocytes with associated inflammation. Autoimmune disease has for many years been thought of as a chronic viral-like disease, however no virus has to date been isolated as an initiator of these types of diseases. These diseases include systemic lupus (SLE), post-radiation syndrome, and a variety of autoimmune kidney diseases, etc. Features of some autoimmune diseases are the presence of hypergammaglobulinemia, elevated IgE and eosinophilia as described above in FIG. 1 step 4. This result may occur as the by-products of a compensatory TH1 to TH2 shift when the body attempts to reestablish Balanced Macrophage Activation.

Allergic reactions: The most serious allergic reaction is asthma wherein overstimulation of step 2 with environmental antigens in the lung leads to inappropriate local macrophage inflammatory changes and T cell activation in lung tissues. These lung tissues are harmed by inflammatory mediators produced in step 3. Normally lung macrophages constitutively have the Alternative Macrophage Activation Pathway induced) (as shown in step 5) and they therefore are less susceptible to steps 2 and 3 as shown in FIG. 1. However, in patients with allergies these reactions (steps 2& 3) are allowed to occur. Asthmatic patients also have a TH1 to TH2 shift with associated eosinophilia. This reaction is predicted by the Balanced Macrophage Activation theory to be compensatory when it attempts to shift lung macrophages from steps 2 & 3 through 4 into step 5.

Immune deficiency associated bacterial and fungal infections: If steps 2 and 3 from FIG. 1 are increased, over time there will be fewer cells in steps 5 and 1 capable of phagocytosis and reinitiation of immune responses. The decreased number of cells capable of phagocytosing bacteria and fungus makes patient survival in the presence of immunodeficiency quite problematic. Antibiotic therapy directed against bacteria and fungus works inefficiently in vivo unless the invading organisms have been phagocytosed by macrophages or granulocytes. The most commonly used antifungal drug, amphotericin B, does not work at all unless fungus has been engulfed by a phagocytic cell. Patients with advanced HIV disease are susceptible to invasive fungal infections mostly because of inefficient phagocytosis. A parallel disease process is induced in patients with organ transplants who receive cyclosporin A and Prednisone for treatment of graft rejection. These patients are immunosuppressed and if they develop invasive bacterial or fungal infections will have their macrophages shifted toward steps 2 and 3 and similarly cannot recycle and achieve Balanced Macrophage Activation, which would allow phagocytosis and reinitiation of immunologic responsiveness.

Chronic wounds: The best example of this class of disease is observed in patients with diabetes or those who are bedridden. Chronic diabetic and pressure ulcers develop and macrophages within those wounds exhibit changes consistent with step 3 in FIG. 1. Goerdt et al., *Immunity* 10: 137–142 (1999). Wounds will not heal if step 3 cannot be shifted through step 5 wherein angiogenic factors are produced to allow blood vessel growth and healing. Similarly if macrophages within a chronic wound have been shifted from step 1 to 3, phagocytic cells will not be present to allow clearance of dead and dying material within wounds so as to speed the healing process.

Cancer: A variety of cancers are outgrowths of chronic inflammation. Examples include lymphoma, which represents outgrowths of antigen-overdriven lymphocytes, and prostate cancer, which evolves from chronic prostatitis. In both cases steps 2 & 3 provide chronic growth stimuli.

In Vitro Studies of WF10 Activity on Immune Function:

WF10 completely blocked antigen activation of T cell responsiveness at levels easily achievable in vivo. McGrath et al., *Transplantation Proceedings,* 30: 4200–4204.(1998). This inhibition of T cell activation only occurred when T cells and macrophages were placed together with the foreign antigen, and occurred instantly or even when added at day 6 of a 7-day T cell activation assay. These data suggest that WF10 is extremely potent at inhibiting processes fundamental to normal T cell activation as shown in step 2 for FIG. 1.

WF10 caused downregulation of inflammatory cytokine production by inflammatory macrophages as described in step 3 for FIG. 1. McGrath et al. Abstract #2046, Keystone Symposia on Molecular and Cellular Biology, Park City, Utah, Mar. 13–19, 1998. Studies are currently underway to test whether WF10 causes upregulation of AMAC-1, thereby converting step 3 to 5 and completion of the BMA cycle in vitro.

The use of WF10 to Achieve BMA in Vivo:

WF10 and Oxoferrin have been used extensively for many years to treat chronic disease in humans. Oxoferrin was approved for topical use in chronic wounds in the late 1980's. To date Oxoferrin has been successful in inducing rapid healing of chronic wounds including diabetic and pressure ulcers. Oxoferrin is thought to work through achieving Balanced Macrophage Activation with associated upregulation of angiogenic factors and macrophage phagocytosis. WF10 was approved in Thailand for systemic use in 1997 for treatment of post-radiation syndrome (PRS). Post-radiation syndrome occurs as a late complication in organs that have received X-ray therapy. Up to 15% of patients who have had lower abdominal irradiation for cervical or prostate cancer develop PRS associated bleeding from the bladder and rectum 6 months to 10 years after that radiation. Histologic analysis shows that the bleeding is caused by a local autoimmune process within the small arteries (endarteritis). This leads to death of tissues within the radiation field and causes bleeding, for example, into the bladder or rectum. Patients sometimes respond temporarily to steroids. However, in studies performed in Thailand there was nearly a 100% complete response rate to systemic administration of WF10 in women with hemorrhagic cystitis secondary to post-radiation syndrome. Unlike steroid treatment, which is associated with some symptomatic relief, WF10 administration to date has been curative for patients with post-radiation syndrome.

Advanced clinical studies of WF10 currently are underway in the United States for treatment of patients with HIV disease. Patients who received two cycles of WF10 showed chronic immunologic changes consistent with induction of Balanced Macrophage Activation. Herndier et al, Abstract #22417, 12$^{th}$ World AIDS Conference, Geneva, Jun. 28–Jul. 3, 1998. Patients with HIV disease, a chronic viral infection, typically show inappropriate elevated T cell activation and decreased rates of macrophage phagocytosis in end-stage disease. In Phase II studies conducted at San Francisco General Hospital, WF10 administration was associated with dramatic down-regulation of all inappropriately elevated immunologic activation markers with up-regulation of macrophage phagocytosis in patients who had low baseline levels of phagocytosis at the initiation of study. These results were consistent with induction of Balanced Macrophage Activation and will lead to further in vitro studies to test components of the Balanced Macrophage Activation theory.

In conclusion, it appears that diseases affecting Balanced Macrophage Activation are common and that many of the side effects of chronic disease occur because of toxic side effects mediated by macrophages accumulating in any one of the steps described above. Currently, WF10 is the only new drug in clinical development that may affect Balanced Macrophage Activation and might be expected to change the clinical outcome of the diseases in sections A through F described above.

The use of an aqueous solution containing a stabilized chlorite solution for treating wounds and infections is known in the art. U.S. Pat. Nos. 4,507,285 and 4,725,437, the disclosures of which are incorporated by reference herein in their entirety, and EP 0 200 157, the disclosure of which also is incorporated by reference herein in its entirety, describe the use of a stabilized chlorite solution in stimulating the wound healing response in humans, as well as in treating infections caused by parasites, fungi, bacteria, viruses and/or mycoplasma. Kühne et al., European Patent No. 200,156, the disclosure of which is incorporated by reference herein in its entirety, describes the use of a stabilized chlorite solution in conjunction with radiation therapy to aid in repairing damaged irradiated tissue and reducing side effects.

A preferred embodiment of the treatment of this invention entails administration to a mammal in need thereof, an aqueous solution of a product that has been termed "tetra-chlorodecaoxygen anion complex," commonly abbreviated as "TCDO." This substance can be prepared using the procedures described in Example 1 of U.S. Pat. No. 4,507,285 ("the '285 patent"), and is a water clear liquid, miscible with alcohols, and has a melting point of −3° C. The Raman spectrum shows bands of 403, 802 (chlorite) and 1562 cm/$^{-1}$ (activated oxygen). The skilled artisan will recognize that any chemically stabilized chlorite solution can be used in the methods of the present invention, and that the scope of the invention is not limited to use of the product described in the '285 patent.

The present invention, thus generally described, will be understood more readily by reference to the following examples, which are provided by way of illustration and are not intended to be limiting of the present invention. In the examples, "WF10" denotes an aqueous stabilized chlorite solution.

EXAMPLE 1

Methods

Sample Preparation

Mononuclear cells (MNC) were isolated on a Histopaque™1077 density gradient using Leuco Sep tubes (#227290, Greiner Labortechnik, Frikenhausen, Germany) and 2×10$^6$ cells were resuspended in RPMI 1640 with 10% FCS. Cultures were stimulated either with a mitogenic anti-CD2 mixture (AICD2M1, AICD2M2 final concentration 1 µg/ml each and 11F1 300 ng/ml), anti-CD3 (OKT-3, 100 ng/ml) or 10 ng/ml PMA and 0.5 μg/ml ionomycin. Unstimulated and stimulated cultures were incubated in the presence or absence of WF10 at a final concentration of 1:300 for 3 hrs at 37° C. in 7% $CO_2$. Cells were harvested, resuspended in 200 μl PBS and 400 μl of High-Pure lysis solution was added. Resulting lysates were stored at −70° C. After thawing at 37° C. for 10 minutes, RNA was extracted using a total RNA isolation kit and RNA was eluted from the spin column in a volume of 50 μl. An aliquot of 8.2 μl RNA was reverse transcribed using AMV-RT and oligo-(dT) as primer (cDNA synthesis kit). As a control, a reaction was performed without reverse transcriptase (no-RT control). After termination of cDNA synthesis the reaction mix was diluted to a final volume of 500 μl and stored at −20° C. until PCR analysis.

LightCyder® PCR

Target sequences were amplified using LightCycler® Primer Sets (Search-LC, Heidelberg, Germany) with the LightCycler FastStart DNA Sybr Green 1 Kit (Roche Diagnostics, Indianapolis, Ind.) according to the manufacturer's protocol. Input was normalized by the average expression of the four housekeeping genes β-actin, HPRT, G6PDH and Cyclophilin B.

Overview of Study Design

Eighteen HIV-infected adults with CD4+ counts greater than 50 cells/$mm^3$ treated with approved anti-HIV medications are enrolled in an open-label, single center study. Participants are involved in the primary phase of the study for approximately 12 weeks. Patients are stratified into two cohorts of nine patients: nine patients have CD4+ counts>300 cells/$mm^3$ and nine patients have CD4+ counts>50 and <300 cells/$mm^3$. Only patients with a viral load of <20,000 copies/mL are enrolled in the study. Enrollment is limited to nine patients with plasma HIV RNA below the limit of assay delectability.

After screening evaluations are completed, eligible patients attend study visits on Days 1, 2, and 4. From Days 8 through 12, patients receive one cycle of WF10 0.5 mL per kg/bw diluted into 250–500 mL normal saline administered by intravenous infusion. Patients then attend study visits on Days 15, 17, 19, 22, 24, and 26.

From Days 29 through 33, patients receive a second cycle of WF10 0.5 mL per kg/bw diluted into 250–500 mL normal saline administered by intravenous infusion. Patients then attend study visits on Days 36, 38, 40, and 47 (final visit). Patients have a 48-hour window in which to return for the final visit on Day 47.

Immune function, measured on days 1, 8, 11, 15, 22, 29, 31, 40 and 47, is defined as the measurement of phagocytic index using fluorescein-labeled *E. coli*, T cell activation with phytohemagglutinin, lymphocyte immune phenotyping (detecting CD3, CD4, CD8, CD14, CD20, CD28, CD38, CD56, CD69), DR, TNF and monocyte quantitation.

The health status of all patients is followed up by monthly telephone calls for one year after Day 47.

Results

Clinical Trial

Of the patients who completed the 47 day study, seven had initial CD4 counts<300/μl, and those patients showed the most dramatic immunologic parameter response to two 5 day cycles of i.v. WF10. CD4 and CD8 counts increased significantly and the CD8 cell increase was completely reflected by an increase in the CD8/38 negative subset. There was an overall dramatic in median CD38 expression with no associated change in HIV viral load during the course of this trial. Other measures of immunologic activation were similarly decreased with an observed significant drop in CD14/DR, CD20/DR and CD4/38 mean levels of cell associated fluorescence.

Gene Expression Analysis of WF10 Trial PBMC

PBMC associated inflammatory gene expression was evaluated on frozen and subsequently extracted cell preparations using Lightcycler based technology. FIG. 2 shows relative levels of a series of proinflammatory genes(to internal housekeeping genes, actin, G6PD, CPB, HPRT) in a patient(#14) who had a 50% decrease in the CD8/38+ cell subset compared to a patient(#15) who had no change of CD8/38 during the 47 days of the trial. The gene expression levels in patient 15 are shown in FIG. 3. There was an overall highly significant correlation between decrease in CD8/38 level and the change in expression of macrophage proinflammatory genes such as those shown in FIG. 2.

In Vitro Effects of WF10 on PBMC and CD14 Cell Gene Expression

WF10 was tested in vitro on PBMC's exposed to anti-CD2, anti-CD3 and PMA/ionomycin to determine effects of the drug on T cell activation. WF10 was used at a final concentration of 1:300, a dose easily achieved during the clinical trial and PBMC's were harvested three hours and affinity purified CD14 cells 18 hours later for RNA extraction and RT-PCR. WF10 effects on 11 normal blood donor PBMC's were expressed as LC-Index which represents up to a 5 fold change from baseline un(WF10) treated but stimulated specimens. A consistent down regulation of induced lymphostimulatory cytokines IL-2 and IL-17 was observed, with a consistent pattern of IL-1β, IL-8, MIP-1a and thioredoxin (TRX) upregulation. Because the upregulations appeared to be macrophage inflammatory mediators, purified CD14 cells were exposed to 1:300 WF10 for 18 hours and evaluated for increased gene expression. Three of the seven CD14 preparations had an approximate decrease in the 4 housekeeping gene levels of 90%. Three CD14 specimens also had dramatic upregulation of the 4 apoptosis genes evaluated and parallel PI uptake studies confirmed CD14 cell apoptosis occurring in those cultures. The gene expression levels of PBMC's used for the macrophage studies before they were treated with WF10 also were determined. It was observed that those specimens that became apoptotic had significantly higher levels of pretreatment inflammatory gene expression than those that did not undergo apoptosis.

WF10 Treatment In Vitro Leads to AMAC-1 Upregulation

Apoptotic cells are the most potent stimulus for macrophages to under alternative (anti-inflammatory) activation and phagocytosis. Alternative activation has been associated with induction by the Th2 cytokine IL-4 and causes a complete block in inflammatory gene expression and antigen induced T cell activaton. Purified macrophages were exposed to a 1:200 dilution of WF10 and AMAC-1 (specific for the alternative pathway, AMAP) gene expressioin was assessed up to 21 days later. WF10 dramatically augmented the AMAC-1 expression induced by macrophage treatment with IL-4.

These data suggest that WF10 administration changes expression of macrophage proinflammatory gene expression in a pattern that parallels changes in CD8/38 levels in vivo. In vitro, WF10 caused dramatic changes in a wide variety of immunologically active genes leading to apoptosis in CD14 cells in a subset of preactivated patient specimens and consistent down regulation of lymphostimulatory genes in PBMCs. It is apparent that WF10 regulates inappropriate inflammation associated with chronic inflammatory diseases such as HIV disease through overactivation induced CD14 cell death with compensatory induction of the alternative (anti-inflammatory) pathway of macrophage activation.

In conclusion, the studies described above demonstrate that

1) WF10 administration to HIV+ patients (<300 CD4 cells/µl) was associated with significant:
   a) Increase in CD4, CD8, CD8/38-cell numbers
   b) Decrease in CD20/DR, CD14/DR, CD4/38 mean fluorescence/cell
   c) Decreased PHA activation
2) Lightcycler system RT-PCR of PBMC's showed drug-associated down regulation of macrophage inflammatory gene expression (TNF-α, etc.).
3) In vitro studies of WF10 effects on normal PBMC (3 h) and CD14 (18 h) cells showed:
   a) Activated PBMC's: Down regulation of lymphostimulatory cytokines IL-2 and IL-17. Upregulation of macrophage inflammatory genes as well as the anti-apoptotic (antioxidant) gene thioredoxin (TRX)
   b) Cultured CD14 cells: Upregulation of apoptotic genes (BAX, BCL-X1, CD95, CD95L) in specimens containing elevated pre-treatment levels of inflammatory genes with associated apoptotic cell (CD14) death.
4) WF10 caused late upregulation of the alternative macrophage activation gene AMAC-1 in isolated CD14 cells.
5) Without being bound by any theory, the inventors believe that WF10 induction of macrophage cell death in specimens containing elevated inflammatory gene expression leads to compensatory AMAP induction in macrophages in response to the acute apoptosis of inflammatory macrophages. Accordingly, WF10 causes downregulation of inflammation through acute upregulation of inflammatory gene expression, cell death through apoptosis, downregulation of lymphostimulatory genes and compensatory macrophage differentiation change to the AMAP, anti-inflammatory pathway.

These observations show that WF10 caused reversal of pathologic inflammation (associated with HIV disease progression) in vivo which over time would be expected to show a long term clinical benefit. The change in immunologic state was documented through use of the quantitative gene expression technique. This test would be utilized in the long term care of treated patients to rapidly identify the return of a pathologic state requiring further WF10 therapy.

EXAMPLE 2

Summary

Peripheral blood mononuclear cells were obtained from the 9 patients described in FIG. 4, as well as from 20 normal blood donors. Gene expression was assessed for baseline as well as PMA/ionomycin stimulated cells as described above. Quantitative evaluation was based on use of 2 housekeeping genes (β-Actin, CPB) to serve as controls for overall cellular gene expression. "Test" gene expression was subsequently normalized to a standard "housekeeping gene" control level. Thirteen genes associated with macrophage and T cell activation were selected for evaluation in this study because of their function in primary immunologic responses and chronic inflammation. The genes were IL-1, IL-2, IL-4, IL-8, IL-10, IP10, MCSF, TNFα, γ-IFN, MIP-1α, MIP-2α, MRP-14, and TGF-β. Normal values for housekeeping genes as well as inflammatory genes were established by evaluating gene expression patterns from 20 normal blood donors (see FIG. 5).

Baseline gene expression was assessed in the patient with acute HCV infection. The quantitative analysis is shown in FIG. 5 as a gene expression score (GES) wherein the quantitative value obtained for each gene was given a score based on its ratio to the mean normal expressed gene level determined in the 20 normal blood donors. The highest level of gene expression observed in the acutely infected patient was the IP-10 gene, known to be induced specifically by γ-interferon. Associated with this elevation of IP-10 was the expected elevation of γ-interferon as well as elevation of the majority of macrophage inflammatory genes assessed (for example, GM-CSF and TNF-α). Genes expressed at baseline/normal values included IL-2, IL-4, IL-8, and IL10. Notably, this gene expression pattern was observed in unstimulated cells isolated from patient blood and not liver or lymph node.

The average gene expression values from blood of the 8 chronically infected patients showed a pattern of gene expression similar to the acute infection specimen consistent with an ongoing immunologic response. The actual GES values varied widely from patient to patient with chronic HCV infection, however. The average values for each gene are shown in FIG. 5. The actual gene expression values and GES are shown in FIG. 6A (baseline) and FIG. 6B (PMA induced). This ongoing response detected in the blood, if present within the liver, could lead to progressive inflammatory damage consistent with that observed in progressive HCV liver disease.

Earlier studies using liver biopsy analysis predicted that T cell hyperactivation would be observed in patients with HCV disease. See Burgio et al., *Hepatology* 27:1600–6 (1998); McGuinness et al. *Gut* 46:260–9 (2000). To test this prediction, peripheral blood monouclear cells from acute and chronic HCV disease patients was stimulated with PMA and ionomycin. The gene expression pattern observed in the patient with acute HCV infection (shown in FIG. 7) was unexpected. Thus the IL-2 and IL-10 gene expression induced in the acutely infected patient was dramatically lower than control values (outside of normal range of GES) suggesting a substantial inhibition of T cell activation associated with acute HCV infection. This inhibition of T cell activation and inhibited γ-interferon production was coupled with persistent elevation in macrophage inflammatory cytokine as well as chemokine genes, such as IP-10, that normally are induced by γ-interferon. This observation suggests that the IP-10 values observed in FIG. 5 along with an elevation of γ-interferon gene expression may not have been the product of T cells as the inducibility of this gene is dramatically inhibited. The only other source of interferon gene expression in blood cells other than T cells would theoretically be the natural killer cell population that also is known to be active in initiating immune responses in virally infected patients. Like the inhibition of T cell activation observed in acute HCV infection, the average GES of the 8 patients with chronic HCV infection showed a pattern of inhibited T cell activation and chronic macrophage activation.

Figure 7:
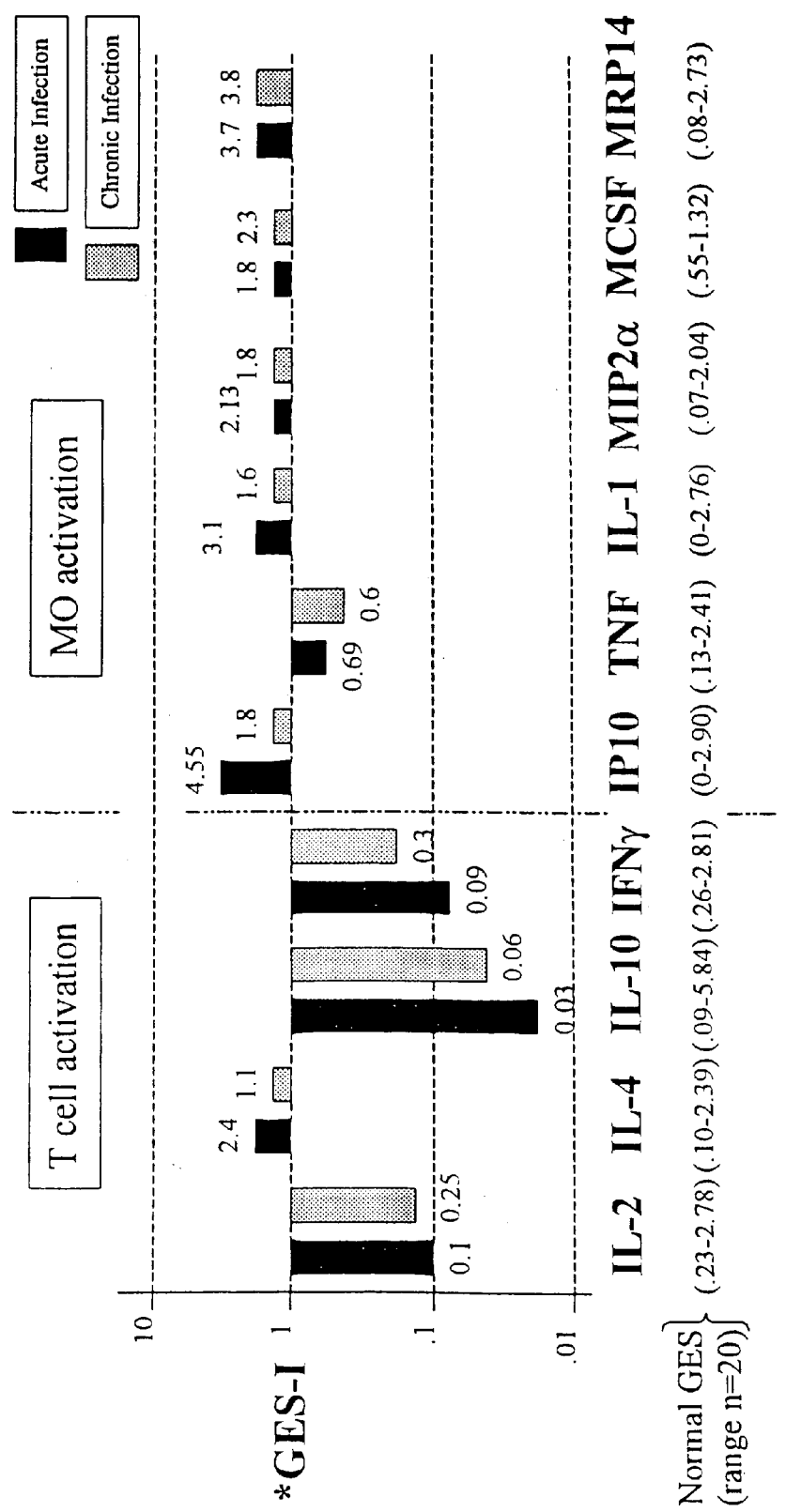
FIG. 7 shows induced gene expression in PBMCs obtained from acute versus chronic HCV infected patients.

The data shown in FIGS. 6B and 7 contrast with prior reported experiments in patients with HCV liver disease that showed elevation of IL-2 levels and hyperactivity of T cells at the protein level. See Martin et al., *Cytokine* 11:267–73 (1999). To determine whether the observed gene expression patterns would correlate with degree of liver inflammation pathology, the corresponding liver biopsies were read and given inflammatory grade scores using standard assessment criteria. FIG. 8 shows the correlation between liver inflammation score and a scoring system based on utilizing GES values from inflammatory genes as determined in the current study. (FIG. 9) A high degree of correlation was found between the MGES (multiple gene expression score) and the degree of liver inflammation.

The degree of histologic liver inflammation was shown to be associated with the induced gene expression analysis. (FIG. 10) In early stage I disease, the strongest inhibition of induced gene expression was observed. During progression of liver inflammation that degree of inhibition gradually reverses, and by stage III inflammation the degree of gene activation was elevated, consistent with prior reports. Induction of IL-10 expression was persistently low even in late stage patients (FIG. 6B).

To test the relationship between the MGES evaluations and the current standard of care measurements (i.e., the ALT blood measurement and HCV quantitative viral load measurement), the ALT values and HCV viral loads for each of the patients shown in FIG. 4 were correlated with degree of liver inflammation similar to the studies shown in FIGS. 8 and 10. Neither the ALT measurement ($r^2$:24) nor the viral load quantitation ($r^2$:0.15) showed correlations with liver biopsy inflammation score, in marked contrast to MGES ($r^2$:0.94 and 0.78 for FIGS. 8 and 10 respectively).

These data demonstrate a new testing system for evaluation of patients with HCV disease. The high degree of correlation of blood based gene expression patterns with liver inflammation allows staging of patients with HCV infection. In particular, the use of rapid RT-PCR methods provides a clinical parameter for assessing the degree of liver inflammation in situ that is faster, less dangerous and less expensive than prior methods.

Materials and Methods

Immune Activation Gene Expression in PBMC from Patients with Acute and Chronic HCV Infection.

Blood specimens were obtained from 1 patient with acute infection and the 8 patients described in FIG. 4. After Ficoll Hypaque separation the PBMCs were placed at 37° in RPMI 1640 with 10% fetal calf serum for 3 hours prior to washing and RNA extraction. The same procedure was performed on blood obtained from 20 normal blood bank donors seen in the Heidelberg, Germany, University Blood Bank. cDNA was synthesized and LightCycler based PCR performed as described above. In each specimen, 4 internal housekeeping genes were included in the RT-PCR analysis; these included the β-actin, HPRT, CPB, and G6PD genes. These 4 genes were utilized to standardize the amount of RNA contained in each specimen and all gene expression scores (GES) were determined utilizing RNA copy numbers based on the internal standardized housekeeping gene copy number normalized data. Based on the standardized copy number of housekeeping genes, a calculated copy number was derived for each of the genes shown in FIG. 6.

Thirteen genes were evaluated utilizing PCR primers (Search-LC, Heidelberg, Germany). The mean gene expression value obtained for 20 normal blood donors was established as a gene expression score of 1 for each of the 13 genes evaluated. Data shown in FIG. 5 represent the deduced copy number of the acute (A) and mean of the 8 chronic (C) HCV infected patient blood specimens. Below each value shown graphically in FIG. 5 is the GES range of the 20 normal blood donors from the absolute lowest to the highest of the 20 values. The data plotted in FIG. 5 represent a single determination of gene expression from all patients, with 1 representing an acute infection (A) and 8 patients combined representing the mean value from chronically infected patients. The gene expression values obtained from the chronically infected patients were widely variable and values are shown in FIG. 6.

Induced Gene Expression in PBMCs Obtained From Acute Versus Chronic HCV Infected Patients.

Blood was obtained as described above from patients with acute and chronic HCV infection as well as 20 normal blood donors. PBMCs were isolated, and placed into culture at 37° with PMA and ionamycin as previously described to induce acute T cell activation. After 3 hours of incubation the cells were harvested, RNA extracted, and LightCycler-based PCR performed as described above. The GES shown in FIG. 7 was calculated based on normalization of gene expression based on housekeeping gene expression. The data shown in FIG. 7 represent a GES for the acute and mean of the 8 patients with chronic HCV infection compared to the mean of the GES calculated from the 20 normal blood donor specimens. Also shown below FIG. 7 is the range from the lowest to the highest values for each of the genes evaluated for the 20 normal blood donor patients. The data shown in FIG. 7 are broken into 2 categories: genes representing T cell activation as compared to genes representing macrophage activation. The acute infection (A) is compared in FIG. 10 to the mean value of the 8 patients with chronic HCV infection. The values for the chronically infected patients were highly variable and are shown in FIG. 6B.

Multigene Expression Score in Unstimulated PBMC of Patients With HCV Disease.

The gene expression values shown in FIG. 6 with the deduced GES values were stratified based on the liver inflammation score obtained independently from a pathologist uninvolved in the gene expression evaluation. A multiple gene expression score (MGES) was determined utilizing gene expression values from the following genes from the patients shown in FIG. 4 (TNFα, IP10, MIP-2α, interferon-γ, and MRP14). The GES of each patient's expressed gene involved in the MGES calculation is shown in FIG. 9. The MGES calculated scores for each patient were then plotted based on a liver inflammation score determined by independent pathologic evaluation and this data was plotted and are shown in FIG. 8. The 20 normal patients were also given MGES scores represented in the figure as normal range which showed MGES from 0 to 2 with a mean of 1. Patient with acute HCV infection is shown with an MGES score of 10. The statistical relationship between the MGES score and liver inflammation score is shown as an $r^2$ value.

Multigene Expression Score in Unstimulated PBMC of Patients With HCV Disease.

Similar to the MGES procedure utilized for data shown in FIG. 8, an MGES was determined based on the induced GES scores as shown in FIG. 9. MGES determinations were based on the calculated GES evaluated for each individual gene being then converted into an MGES score combination, including all 3 genes. The normal range is shown and designated normal range with the mean of 1 with the range from −3 to 0. Acute HCV infection is shown with a calculated MGES of −2.5. The statistical relationship between the MGES score and liver inflammation score is shown as an $r^2$ value.

While the invention has been described in detail with reference to the examples and particularly preferred embodiments, those skilled in the art will appreciate that various modifications can be made to the invention without departing from the spirit and scope thereof. All documents referred to above are incorporated by reference.

What is claimed is:

1. A method of evaluating a clinical outcome for a patient suffering from an inflammatory disorder, HIV infection, or allograft rejection, wherein said patient is being treated with a stabilized chlorite solution or is being considered for treatment with a stabilized chlorite solution, comprising the steps of:

(a) measuring the levels of intracellular expression of a related to an inflammatory disorder, HIV infection, or allograft rejection preselected set of genes in cells in a clinical specimen obtained from said patient;

(b) comparing said levels of expression against a set of reference expression levels, wherein a an increase or decrease in the level of expression of one or more of said preselected set of genes is indicative of clinical outcome for said patient.

2. A method according to claim 1, wherein said stabilized chlorite solution is an aqueous solution of tetrochlorodecaoxygen (WF-10).

3. A method according to claim 1, wherein said clinical specimen is a sample of blood, tissue, or cerebrospinal fluid.

4. A method according to claim 1, wherein said clinical specimen is a sample of blood.

5. A method according to claim 1, wherein said preselected set of genes comprises at least three proinflammatory cytokines.

6. A method according to claim 5, wherein said at least three proinflammatory cytokines are selected from the group consisting of Tumor Necrosis Factor-$\alpha$ (TNF-$\alpha$), Interleukin-6 (IL-6), Interleukin-1 (IL-1), Interleukin-2 (IL-2), Interleukin-4 (IL-4), Interleukin-8 (IL-8), Interleukin-10 (IL-10), Inducible Protein 10 (IP10), Macrophage Colony Stimulating Factor (MCSF), $\delta$-Interferon ($\delta$-IFN), Macrophage inflammatory protein-1$\alpha$ (MIP-1$\alpha$), Macrophage Inflammatory Protein-2$\alpha$ (MIP-2$\alpha$), Mitochondrial Ribosomal Protein-14 (MRP-14), and Transforming Growth Factor-$\beta$ (TGF-$\beta$).

7. A method according to claim 1, wherein said patient suffers from an inflammatory disorder, and wherein said inflammatory disorder is a chronic inflammatory disorder.

8. A method according to claim 7, wherein said chronic inflammatory disorder is selected from the group consisting of chronic hepatitis, hepatitis B, hepatitis C, chronic obstructive pulmonary disease, inflammatory mucosal disease, autoimmune disease, dementia, cardiovascular disease, and cancer.

9. A method according to claim 8, wherein said inflammatory mucosal disease is selected from the group consisting of inflammatory bowel disease, Crohn's disease, and colitis, autoimmune disease, dementia, cardiovascular disease, and cancer.

10. A method according to claim 8, wherein said dementia is AIDS-related dementia or Alzheimer's disease.

11. A method according to claim 9, wherein said cancer is selected from the group consisting of lymphoma, prostate cancer, and colon cancer.

12. A method according to claim 1, wherein said patient suffers from HIV infection, and wherein said HIV infection is AIDS.

13. A method according to claim 1, wherein said clinical outcome is the probability of patient survival after a preselected time interval.

14. A method according to claim 1, wherein said levels of gene expression are measured using a quantitative polymerase chain reaction.

15. A method according to claim 14, wherein the polymerase chain reaction is a reverse transcriptase/polymerase chain reaction.

16. A method according to claim 15, wherein said polymerase chain reaction is carried out using fluorescent detection of the amplification products.

* * * * *

UNITED STATES PATENT AND TRADEMARK OFFICE
CERTIFICATE OF CORRECTION

PATENT NO. : 6,703,202 B2
DATED : March 9, 2004
INVENTOR(S) : Michael McGrath et al.

It is certified that error appears in the above-identified patent and that said Letters Patent is hereby corrected as shown below:

Column 16,
Line 66, after "expression of a" insert -- preselected set of genes --.

Column 17,
Line 1, after "rejection" delete "preselected set of genes".
Line 4, after "wherein" delete "a".

Signed and Sealed this

Eighteenth Day of October, 2005

JON W. DUDAS
*Director of the United States Patent and Trademark Office*